United States Patent

Kayser et al.

[11] 4,354,493
[45] Oct. 19, 1982

[54] THORACIC DRAINAGE UNIT

[75] Inventors: John P. Kayser; John R. Pinkert, both of Madison, Wis.

[73] Assignee: Airco, Inc., Montvale, N.J.

[21] Appl. No.: 200,659

[22] Filed: Oct. 27, 1980

[51] Int. Cl.³ .............................................. A61M 1/00
[52] U.S. Cl. .................................................... 128/276
[58] Field of Search ............... 128/276, 277, 278, 760; 137/205

[56] References Cited

U.S. PATENT DOCUMENTS 3,279,467 10/1966 Hafstra et al. ....................... 128/276
4,036,231 7/1977 Dodge et al. ........................ 128/276
4,085,751 4/1978 Dodge .................................. 128/276

Primary Examiner—Richard J. Apley
Assistant Examiner—J. L. Kruter
Attorney, Agent, or Firm—Roger M. Rathbun; Larry R. Cassett

[57] ABSTRACT

A thoracic drainage unit for removal of fluids from the thoracic cavity of a patient and/or to assist a patient in breathing comprises a collection chamber for receiving the fluids from the patient and an underwater seal located between the collection chamber and the patient. The underwater seal prevents pressure being applied to the thoracic cavity or backflow to that cavity. The water or other liquid for the seal is provided with the collection chamber as a complete unit ready for use. A collapsible bottle has a breakable neck that is readily broken by the user, whereupon the bottle is collapsed to force the liquid therein to create the liquid seal. A baffle is provided to prevent the liquid from reentering the bottle as it reexpands so that the precise needed volume of liquid is retained to create the seal. Also, the water seal is located in a particular location, and the underwater seal chamber is designed such that seal integrity is not lost upon tipping over the drainage unit; and the seal remains viable upon righting the unit. The underwater seal chamber is designed to allow viewing of an air leak from the patient, even through foaming or opaque fluid. Critical measurement area for collected fluids is provided, and hangers that can be used also as floor stand are included with unit.

5 Claims, 7 Drawing Figures

FIG. 3
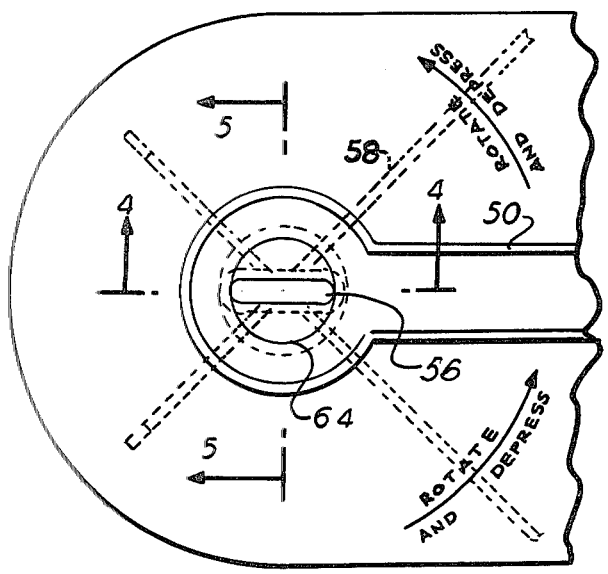
FIG. 4
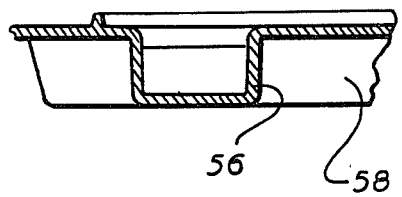
FIG. 6
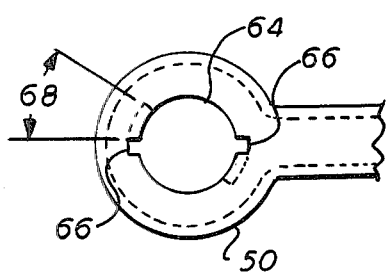
FIG. 5
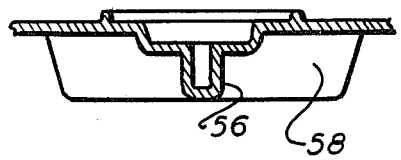
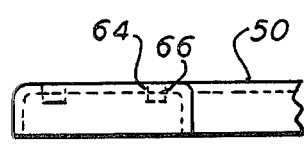
FIG. 7

THORACIC DRAINAGE UNIT

BACKGROUND OF THE INVENTION

This invention relates to methods and devices for carrying out pleural or thoracic drainage of a patient. Such drainage is used to remove gas or air from the pleural cavity surrounding the lungs and also to remove blood or other liquids therefrom. Typically, such drainage is needed after chest surgery or the infliction of a chest wound, a lung puncture, or even from certain diseases.

In any event, such drainage is characterized by the application of very low vacuum since high vacuum could overextend the lungs or cause damage. The pleural drainage device maintains a very slight negative pressure in the pleural cavity, thus assisting in the expansion of the lungs by the patient to thus ease the effort or burden of patient breathing. The low negative pressures used, or present in the pleural cavity may range in the order of 5-20 cm water.

One well known system used to carry out pleural drainage is called the three bottle system, wherein one of the bottles is utilized for the collection of fluids from the patient, a second bottle is used to provide an underwater seal preventing backflow to the patient and still a third bottle used to regulate the maximum amount of vacuum that can be applied to the pleural cavity.

Various devices are currently on the market that combine the function of two or even three bottles of the aforementioned system.

The purpose of the collection bottle is, of course, obvious since it is merely a container or chamber for receiving the fluids that are removed from the patient via use of vacuum. The underwater seal bottle has the function of a check valve and prevents backflow to the pleural cavity or buildup of pressure in such cavity. Although the specific features of an underwater seal will be later explained, it is suffice to say that such seals are preferable in connection with pleural drainage inasmuch as they are functionable at extremely slight vacuum levels and flows used with pleural drainage and have no moving parts that could malfunction through sticking or other physical disabilities. As will be seen, a dangerous situation could occur in the event the check valve function in a pleural drainage system were to stick in the closed position.

In present devices combining a collection chamber and an underwater seal, the liquid, normally sterile saline solution, that is used to effect the seal itself, is added to the device just before the pleural drainage unit is utilized. Thus, the unit itself is manufactured and sold without the liquid, and when it is desired to be put into use, a volume of sterile liquid must be carefully measured and introduced, normally by pouring the same, into the pleural drainage unit to create the water seal. Difficulties occur in the possibility of spillage, thus making the desired volume inaccurate, the accuracy or inaccuracy of the volume measurement itself, and the ready availability of a sterile liquid at the location where the unit is to be utilized.

Other features of presently marketed pleural drainage units include the need to provide a water seal having a small volume such as to reduce dead air space yet, at the same time, the collection chamber should be of sufficient size as to receive fluids for a considerable period of time before becoming filled.

In addition, a desirable feature in pleural drainage units is the visibility of the water seal so that personnel attending to the patient can visually perceive bubbles in the unit evidencing good pressure within the pleural cavity during exhalation and thus provide an indication of the strength of the patient's breathing.

Accordingly, the present invention is concerned with overcoming certain problems presently existing in methods and apparatus to carry out pleural drainage, particularly with respect to the introduction of a liquid into the unit to form an underwater seal. The unit can be tipped over without losing the integrity and function of the underwater seal upon righting thereof. The underwater seal function of the unit is visible and does not introduce significant dead air space into the overall unit.

SUMMARY OF THE INVENTION

In accordance with the invention, a pleural drainage unit is provided wherein the unit itself is manufactured, sold and shipped with its own supply of liquid for an underwater seal. The pleural drainage unit has a collection chamber adapted to receive fluids drained from the patient and is adapted to be connected to a regulated vacuum source.

The underwater seal is located in the drainage unit intermediate the collection chamber and the patient, and contains a relatively small volume such as to minimize dead air space. As the unit is sold, the underwater seal container is empty, however, a collapsible bottle is provided with each pleural drainage unit and is prefilled during manufacture with a predetermined volume of a sterile liquid, normally saline solution. The prefilled bottle has a breakable neck such that the neck is readily severed from the bottle, thus opening the sterile liquid to various passageways in the drainage unit leading to the underwater seal space. The bottle is then collapsed and the liquid contained therein is directly forced into the underwater seal container, thereby assuring the maintaining of sterility of the liquid and also avoiding any possibility of spillage that could affect the predetermined volume of the fluid making up the underwater seal.

A baffle means is provided such that once the bottle is collapsed to force liquid into the drainage unit, the bottle may, by its own memory, again expand without withdrawing any of the liquid from the underwater seal chamber. Thus, sufficient liquid from the bottle enters the unit to be used for the underwater seal.

In the preferred embodiment, the collapsible bottle is affixed to the pleural drainage unit in the manufacture thereto and the breakable neck is constrained such that a twisting of the bottle severs the neck from the bottle to allow the contents to be directed to the underwater seal.

By positioning the underwater seal and the liquid that creates the same at a particular position and in a particular configuration, the integrity of the seal can be maintained even when the drainage unit is inadvertently tipped over and then righted.

BRIEF DESCRIPTION OF DRAWINGS

The invention is diagrammatically illustrated by way of example in the drawings appended hereto in which:

FIG. 3 is a plan view of that portion of the thoracic drainage unit of FIG. 1 that receives the collapsible container of FIG. 2.

FIG. 4 is a cross-sectional view taken along the lines 4—4 of FIG. 3.

FIG. 5 is a cross-sectional view taken along the lines 5—5 of FIG. 3.

FIG. 6 is a plan view of the upper receiving portion of the portion shown in FIG. 3, and FIG. 7 is a side view of the receiving portion shown in FIG. 6.

DESCRIPTION OF THE PREFERRED EMBODIMENT

Figure 1:
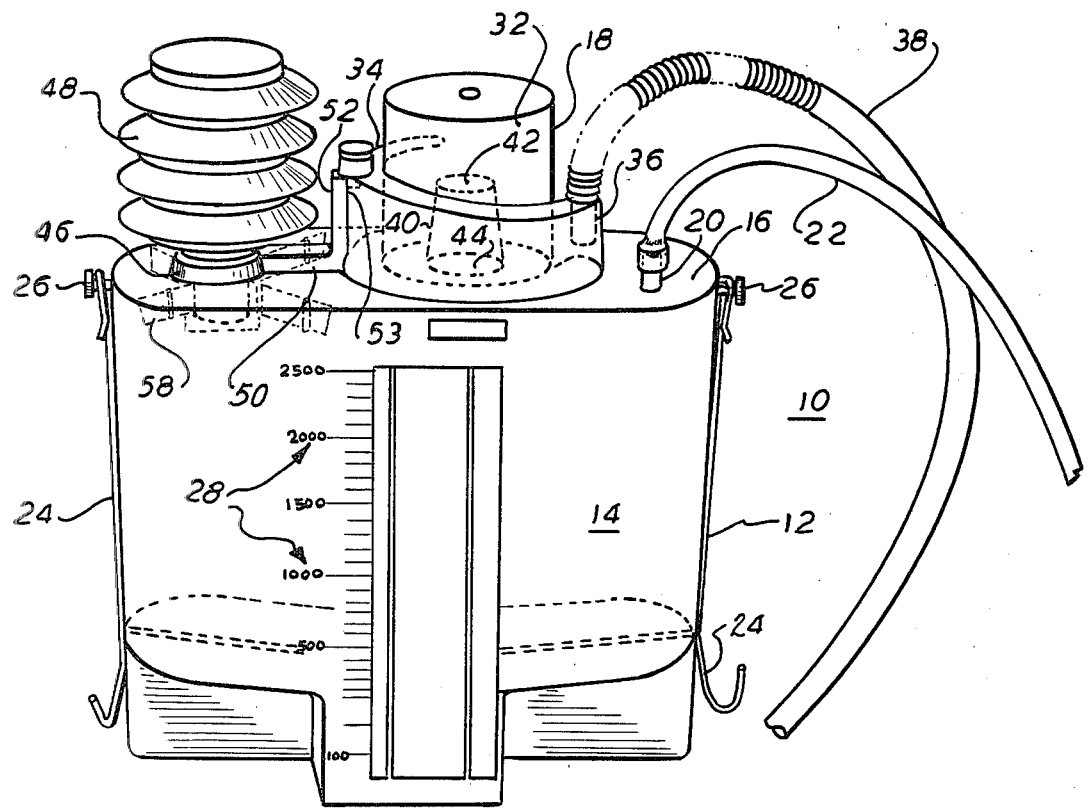
FIG. 1 is an external, perspective view of the thoracic drainage unit constructed in accordance with the present invention.

In FIG. 1, there is shown a perspective view of the thoracic drainage unit 10 constructed in accordance with the present invention. The thoracic drainage unit 10 includes a container 12 within which is a collection chamber 14 for receiving fluids withdrawn from a patient.

The container 12 has a cover 16 enclosing the top of the collection chamber 14 and has mounted thereon a liquid seal chamber 18 which will be later explained in more detail.

A gas outlet 20 extends upward from cover 16 and may be molded integral therewith. The gas outlet 20 is adapted to receiving a tube 22 which is adapted to be connected to a regulated source of vacuum.

The container 12 further may include hooks 24, preferably of metal, and which may be rotated upwardly upon projections 26 so that the thoracic drainage unit 10 may be hung from a suitable stable means such as the patient bed side rail. Indicia 28 is marked on the sidesurface of container 12 so that the amount of fluid within the collection chamber 14 may, at any time, be readily observed.

As stated, a liquid seal chamber 18 is provided above and selectively sealed to the cover 16. As shown, the liquid seal chamber 18 includes an upward cylindrical container 32 within which is formed a water trap chamber. The cylindrical container 32 communicates with and is joined to a spiral chamber 34 extending around a portion of its periphery. A drainage inlet 36 provides a passageway for fluid entering the liquid seal chamber 18 from the patient and which may be connected to a flexible tubing 38 which, in turn, may be connected to a catheter, not shown, adapted to be placed into the thoracic or pleural cavity for the withdrawal of fluids therefrom.

The drainage inlet 36 extends downwardly into the spiral chamber 34 a predetermined distance. A drain 40 is located within the upward cylindrical chamber 32 and, as shown, is conically shaped having an opening 42 at its uppermost point. The lower edge of upward cylindrical chamber 32 is sealed to the cover 16 surrounding an opening 44 in the cover 16 leading into the collection chamber 14.

The thoracic drainage unit 10 also includes a means to fill the underwater seal chamber 18 with a predetermined amount of liquid, and includes a receptacle 46 formed in the cover 16 and which receives a collapsible bottle 48. As will become apparent, the collapsible bottle 48 is sealed and contains a predetermined precise amount of liquid, preferably a sterile saline solution.

A channel 50 extends from receptacle 46 and provides a passageway for liquid from receptacle 46 to the liquid seal chamber 18. As may be seen, the channel 50 has a vertical rise 52. When liquid flowing from receptacle 46 is caused to flow upwardly and over a baffle 53 before entering the liquid seal chamber 18, it cannot return when the collapsible bottle 48 is released.

Figure 2:
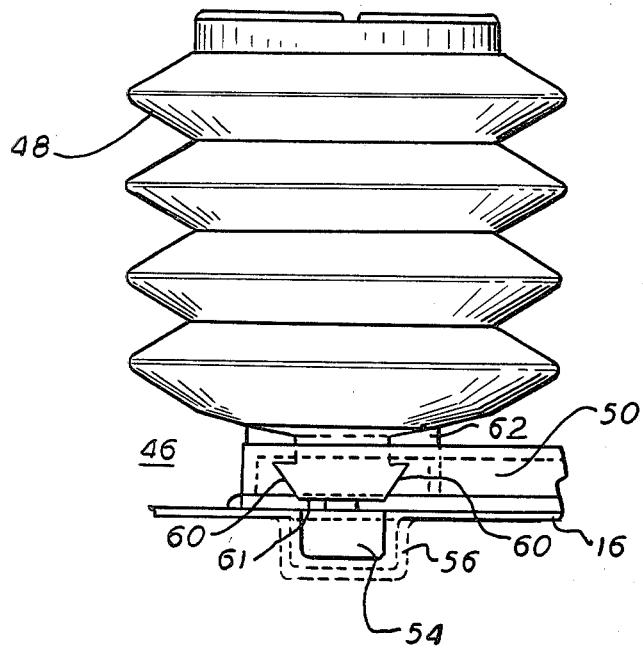
FIG. 2 is a perspective view of a collapsible container used on a part of the present invention.

Turning now to FIG. 2, there is shown a perspective side view showing the collapsible bottle 48 in position assembled within receptacle 46. As will be seen in describing this invention, the entire thoracic drainage unit 10 may be shipped from the supplier with the collapsible bottle 48 assembled to the receptacle 46 or, on the other hand, the thoracic drainage unit 10 may be shipped by itself and the collapsible bottle 48 shipped unassembled, either copackaged or separate from the thoracic drainage unit 10.

In FIG. 2, the collapsible bottle 48 is shown having a flat, downwardly depending tab 54 which fits into a corresponding shaped recess 56 formed beneath the cover 16 and held in position by bracing struts 58 (FIG. 1) when the collapsible bottle 48 is thus positioned within receptacle 46, the tab 54 is rigidly held in position preventing rotation thereof.

The collapsible bottle 48 may be held in its assembled position in receptacle 46 by means of a plurality of projections 60 which underfit within channel 50. A seal 62 surrounds the lower portion of the collapsible bottle 48 and seals against the upper surfacing of the channel 50.

The collapsible bottle 48 has a weak breakable section 61, the purpose for which will be later explained.

In FIG. 3, there is shown a plan view of the receptacle 46 associated with cover 16 and including the channel 50 into which is provided an opening 64 for receiving the collapsible bottle 48 (not shown in FIG. 2). Also shown in FIG. 3 is the recess 56 which receives and holds the tab 54 when the collapsible bottle 48 is fitted into the receptacle 46.

In FIGS. 4 and 5, there is shown, in cross section, views of the recess 56 which receives tab 54 (not shown). The recess 56 is preferably formed with molded plastic bracing struts flange 58 (not shown).

In FIGS. 6 and 7, there is shown, in top and side views, the channel 50 and which is assembled by sealing the channel 50 to the upperside of cover 16 (not shown). As shown, the channel 50 has opening 64 for receiving the collapsible bottle 48 and insert openings 66 into which the projections 60 (FIG. 2) can be fitted. As may now be seen, the preferred collapsible bottle 48 may be inserted into the receptacle 46 by insertion, whereby the lower tab 54 of the collapsible bottle 48 is held firmly within recess 56. The projections 60 (FIG. 2) fit within insert openings 66.

To utilize the thoracic drainage unit 10, therefore, returning to FIGS. 1 and 2, the collapsible bottle 48 containing the predetermined quantity of liquid is twisted through the approximate angle 68 (FIG. 6), thereby severing the tab 54 from the collapsible bottle 48 at the weak breakable section 61 and the liquid may be forced, by physically collapsing the collapsible bottle 48 into channel 50 and thus over baffle 53 into the liquid seal 18, thus filling the same to the precise desired level. As the collapsible bottle 48 re-expands through its memory, the baffle 53 prevents liquid from being redrawn into the collapsible bottle 48 so that the correct amount is retained within the liquid seal chamber 18.

The liquid seal thus formed contains precisely the amount of liquid without the need for measuring and pouring the same into the unit. In addition, by providing the opening 42 in the center of the water trap chamber 32, very little of the liquid is lost into the collection chamber 14 in the event the thoracic drainage unit 10 is inadvertently overturned. Upon righting, therefore, the water seal integrity is maintained, yet, as fluids are drawn into the thoracic drainage unit through flexible tubing 38, those fluids fill the water trap chamber 34 to the height where the fluids flow through openings 40 and 42, thus proceed through the drain 40 and down into the collection chamber 14.

It will now be apparent that there has been described, an improved thoracic drainage device having means for filling its water trap chamber by providing a collapsible container having contained therein, a liquid of predetermined quantity to be supplied for forming the water trap. It should be understood that although the invention has been described with reference to a particular embodiment, modifications thereto may be made without departing from the true spirit and scope of the invention.

What is claimed is:

1. A thoracic drainage device having a collection chamber for receiving fluids from a body cavity to be drained, said drainage device comprising a water trap chamber for receiving the fluids, said water trap chamber further containing a predetermined quantity of liquid, inlet means to said water trap chamber and with means to communicate with the body cavity to be drained, said inlet means disposed within said water trap chamber at a point below the level of said initial quantity of liquid, outlet means from said water trap chamber to carry liquid from said water trap chamber to said collection chamber as said liquid reaches a predetermined level in said water trap chamber, receptacle means carried by said drainage device and means to receive a container containing the initial quantity of liquid, channel means providing a flow path for the liquid received in said receptacle means to said water trap chamber and baffle means in said channel means intermediate said receptacle means and said water trap chamber to prevent any return flow of the liquid from the water trap chamber to said receptacle.

2. A thoracic drainage device having a collection chamber for receiving fluids from a body cavity to be drained, said drainage device comprising a water trap chamber for receiving the fluids, said water trap chamber means to contain a predetermined quantity of liquid, inlet means to said water trap chamber and said means to communicate with the body cavity to be drained, said inlet means disposed within said water trap chamber at a point below the level of said predetermined quantity of liquid, outlet means in said water trap chamber and opening into said collection chamber, said outlet means extending upwardly in said water trap chamber and having an opening at its top to receive liquid from said water trap chamber as said liquid reaches a predetermined level in said water trap chamber and to channel said liquid into said collection chamber, said outlet means being located within said water trap chamber as to minimize liquid entering said opening in the event said thoracic drainage device is tipped from its normal upright position.

3. A thoracic drainage device having a collection chamber for receiving fluids from a body cavity to be drained, said drainage device comprising a water trap chamber means for receiving the fluids, said water trap chamber means to be initially filled with a predetermined quantity of liquid, inlet means to said water trap chamber located at a point within said water trap chamber beneath the level of said initial quantity of liquid, outlet means from said water trap chamber to discharge liquid from said water trap chamber to said collection chamber as said liquid reaches a predetermined level in said water trap chamber, receptacle means on said drainage device, a collapsible bottle containing the predetermined quantity of liquid which interfits and communicates with said receptacle means to discharge the liquid into said receptacle means by collapsing said bottle, channel means providing a flow path for the liquid received in said receptacle to said water trap chamber and baffle means in said channel means intermediate said receptacle means and said water trap chamber to prevent the return flow of the liquid from said water trap chamber to said receptacle.

4. A thoracic drainage collection device as defined in claim 3 wherein said collapsible bottle interfitting retains said collapsible bottle in position in said receptacle means and communicates the liquid with said receptacle means by breaking a portion of said collapsible bottle.

5. A thoracic drainage collection device as defined in claim 3 wherein, said collapsible bottle includes a tab fixed in position within said receptacle, and said tab is broken by rotating said collapsible bottle with respect to said receptacle.

* * * * *